United States Patent
St. Pierre et al.

(10) Patent No.: US 11,071,467 B2
(45) Date of Patent: Jul. 27, 2021

(54) HYBRID PATIENT MONITORING SYSTEM

(71) Applicant: Welch Allyn, Inc., Skaneateles Falls, NY (US)

(72) Inventors: Shawn C. St. Pierre, Skaneateles Falls, NY (US); Ian K. Edwards, Skaneateles, NY (US)

(73) Assignee: Welch Allyn, Inc., Skaneateles Falls, NY (US)

( * ) Notice: Subject to any disclaimer, the term of this patent is extended or adjusted under 35 U.S.C. 154(b) by 1219 days.

(21) Appl. No.: 14/454,225

(22) Filed: Aug. 7, 2014

(65) Prior Publication Data

US 2015/0045679 A1 Feb. 12, 2015

Related U.S. Application Data

(60) Provisional application No. 61/863,817, filed on Aug. 8, 2013.

(51) Int. Cl.
*A61B 5/022* (2006.01)
*A61B 5/0225* (2006.01)
(Continued)

(52) U.S. Cl.
CPC ............ *A61B 5/0225* (2013.01); *A61B 5/024* (2013.01); *A61B 5/02007* (2013.01)

(58) Field of Classification Search
None
See application file for complete search history.

(56) References Cited

U.S. PATENT DOCUMENTS

| | | | |
|---|---|---|---|
| 3,527,204 A | 9/1970 | Lem | |
| 4,313,445 A | 2/1982 | Georgi | |

(Continued)

FOREIGN PATENT DOCUMENTS

| | | |
|---|---|---|
| EP | 838194 A1 | 4/1998 |
| EP | 838194 B1 | 4/2003 |

(Continued)

OTHER PUBLICATIONS

Cappuccio et al., A Prospective Study of Hypertension and the Incidence of Kidney Stones in Men, Journal of Hypertension 1999, 17:1017-1022 (6 pages).

(Continued)

*Primary Examiner* — Meredith Weare
(74) *Attorney, Agent, or Firm* — Lee & Hayes, P.C.

(57) ABSTRACT

A system for monitoring a patient includes a sensor configured to determine a first characteristic and a second characteristic of an at least partially occluded artery. The system also includes a control module in communication with the sensor and configured to determine a hemodynamic parameter of the patient based on the first and second characteristics. The control module is operable in an automatic operating mode and a manual operating mode. The automatic operating mode is characterized by the sensor determining, in response to one or more sensor control signals automatically generated by the control module, the first and second characteristics during at least one of automatic inflation and automatic deflation of a cuff associated with the control module. The manual operating mode is characterized by the sensor determining, in response to manual actuation of a trigger associated with the sensor, the first and second characteristics during at least one of inflation and deflation of the cuff.

28 Claims, 5 Drawing Sheets

(51) Int. Cl.
*A61B 5/024* (2006.01)
*A61B 5/02* (2006.01)

(56) References Cited

U.S. PATENT DOCUMENTS

| | | | |
|---|---|---|---|
| 4,367,751 A | 1/1983 | Link | |
| 4,407,297 A | 10/1983 | Croslin | |
| 4,493,326 A | 1/1985 | Hill | |
| 4,617,937 A | 10/1986 | Peel | |
| 4,671,290 A | 6/1987 | Miller | |
| 4,729,383 A | 3/1988 | Susi | |
| 4,796,184 A | 1/1989 | Bahr et al. | |
| 4,889,133 A | 12/1989 | Nelson et al. | |
| 4,949,710 A | 8/1990 | Dorsett et al. | |
| 5,014,714 A | 5/1991 | Millay et al. | |
| 5,025,791 A | 6/1991 | Niwa | |
| 5,170,795 A | 12/1992 | Ramsey et al. | |
| 5,253,648 A | 10/1993 | Walloch | |
| 5,267,567 A | 12/1993 | Aung | |
| 5,339,818 A | 8/1994 | Baker et al. | |
| 5,348,004 A | 9/1994 | Hollub | |
| 5,349,519 A | 9/1994 | Kaestle | |
| 5,392,781 A | 2/1995 | Phillipps et al. | |
| 5,404,878 A | 4/1995 | Frankenreiter et al. | |
| 5,485,848 A | 1/1996 | Jackson | |
| 5,577,508 A | 11/1996 | Medero | |
| 5,606,977 A | 3/1997 | Ramsey et al. | |
| 5,649,536 A | 7/1997 | Ogura | |
| 5,651,370 A | 7/1997 | Hersh et al. | |
| 5,752,913 A | 5/1998 | Oka et al. | |
| 5,752,919 A | 5/1998 | Schrimpf | |
| 5,758,652 A | 6/1998 | Nikolic | |
| 5,772,601 A | 6/1998 | Oka et al. | |
| 5,791,348 A | 8/1998 | Aung | |
| 5,836,887 A | 11/1998 | Oka et al. | |
| 5,971,932 A | 10/1999 | Okamoto | |
| 6,083,172 A | 7/2000 | Baker et al. | |
| 6,099,476 A | 8/2000 | Engel et al. | |
| 6,168,567 B1* | 1/2001 | Pickering | A61B 5/02208 |
| | | | 600/490 |
| 6,196,974 B1 | 3/2001 | Miwa et al. | |
| 6,236,872 B1 | 5/2001 | Diab | |
| 6,322,516 B1 | 11/2001 | Inukai et al. | |
| 6,322,517 B1* | 11/2001 | Yamamoto | A61B 5/022 |
| | | | 600/490 |
| 6,405,076 B1 | 6/2002 | Taylor | |
| 6,428,481 B1 | 8/2002 | Inukai et al. | |
| 6,443,905 B1 | 9/2002 | Nissila | |
| 6,500,127 B1 | 12/2002 | Inukai et al. | |
| 6,503,206 B1 | 1/2003 | Li et al. | |
| 6,602,199 B2* | 8/2003 | Chen | A61B 5/022 |
| | | | 600/485 |
| 6,656,116 B2 | 12/2003 | Kim et al. | |
| 7,515,961 B2 | 4/2009 | Germanson et al. | |
| 7,678,060 B1 | 3/2010 | Millen | |
| 8,016,765 B2 | 9/2011 | Ramsey | |
| 8,114,026 B2 | 2/2012 | Leschinsky | |
| 8,197,416 B1 | 6/2012 | Shankar | |
| 9,510,760 B2* | 12/2016 | Chen | A61B 5/02225 |
| 2004/0019284 A1 | 1/2004 | Kawaguchi et al. | |
| 2004/0167411 A1 | 8/2004 | Kolluri et al. | |
| 2006/0155196 A1* | 7/2006 | Ramsey | A61B 5/02141 |
| | | | 600/490 |
| 2007/0038129 A1 | 2/2007 | Kishimoto et al. | |
| 2007/0118036 A1 | 5/2007 | Hersh et al. | |
| 2008/0119745 A1* | 5/2008 | Yang | A61B 5/02141 |
| | | | 600/493 |
| 2009/0062664 A1 | 3/2009 | Chang et al. | |
| 2009/0312652 A1 | 12/2009 | Yamakoshi et al. | |
| 2010/0010356 A1* | 1/2010 | Chan | A61B 5/0002 |
| | | | 600/493 |
| 2010/0234742 A1 | 9/2010 | Lin et al. | |
| 2010/0331724 A1 | 12/2010 | Watson et al. | |
| 2011/0066006 A1 | 3/2011 | Banet et al. | |
| 2011/0077535 A1 | 3/2011 | Chen et al. | |
| 2011/0092830 A1 | 4/2011 | Chen et al. | |
| 2011/0160597 A1 | 6/2011 | Lane et al. | |
| 2011/0218447 A1 | 9/2011 | Kinoshita | |
| 2012/0220884 A1* | 8/2012 | Yamashita | A61B 5/022 |
| | | | 600/490 |
| 2012/0226173 A1 | 9/2012 | Quinn et al. | |
| 2013/0261475 A1* | 10/2013 | Mochizuki | A61B 5/02233 |
| | | | 600/493 |
| 2013/0345576 A1* | 12/2013 | Chen | A61B 5/02225 |
| | | | 600/490 |

FOREIGN PATENT DOCUMENTS

| | | |
|---|---|---|
| JP | 06133938 A | 5/1994 |
| JP | 10066679 A | 3/1998 |
| JP | 10137202 A | 5/1998 |
| JP | 10151118 A | 6/1998 |
| JP | 2002191568 A | 7/2002 |
| WO | 1986003114 A1 | 6/1986 |
| WO | 2001050952 A1 | 7/2001 |
| WO | 2005020808 A1 | 3/2005 |
| WO | 2007025341 A1 | 3/2007 |
| WO | 2011110491 A1 | 9/2011 |

OTHER PUBLICATIONS

O'Brien et al., The British Hypertension Society Protocol for the Evaluation of Blood Pressure Measuring Devices, Journal of Hypertension 1993, 11 (suppl 2):543-562 (20 pages).

Goonasekera et al., Random Zero Sphygmomanometer Versus Automatic Oscillometric Blood Pressure Monitor; is Either the Instrument of Choice?, Journal of Human Hypertension (1995) 9, 885-889 (5 pages).

Semi-automatic digital blood pressure arm monitor, adult Source: http//www.shop.gorillascientific.com/Semi-Automatic-Digital-Blood-Pressure-Arm-Monitor-Adult-01-5041.htm? gclid=CIWD57_WkrICFWXhQgod4FIAfg Date Accessed: Sep. 10, 2012.

Elemano digital automatic hybrid blood pressure monitor Source: http://www.ebay.com/itm/ELEMANO-DIGITAL-AUTOMATIC-HYBRID-BLOOD-PRESSURE-MONITOR-/270631061733#vi-content Date Accessed: Sep. 10, 2012.

Taking an Automated and Manual Blood Pressure Reading with the SunTech 247 Source: http://www.suntechmed.com/support/customer-technical-support/video-tutorials/207-taking-an-automated-and-manual-blood-pressure-reading-with-the-suntech-247 Date Accessed: Sep. 10, 2012.

Appel et al., Ambulatory Blood Pressure Monitoring and Blood Pressure Self-Measurement in the Diagnosis and Management of Hypertension, Annals of Internal Medicine, Jun. 1, 1993 vol. 118 No. 11, 867-882.

Owens et al., Diagnosis of White Coat Hypertension by Ambulatory Blood Pressure Monitoring, Scientific Contributions, Hypertension, 1999; 34:267-272 (7 pages).

Michell, Routine Blood Pressure Measurement: application of the standard canine technique in a human, University of London (Royal Veterinary College), Aug. 1996;1(4):385-387.

Kuulasmaa et al., Quality Assessment of Data on Blood Pressure in the Who Monica Project, May 1998, http://www.thl.fi/publications/monica/bp/bpga.htm, Date Accessed: Jul. 12, 2012.

* cited by examiner

HYBRID PATIENT MONITORING SYSTEM

CROSS-REFERENCE TO RELATED APPLICATION

This application claims the benefit of U.S. Provisional Application No. 61/863,817, filed Aug. 8, 2013, the entire disclosure of which is incorporated herein by reference.

TECHNICAL FIELD

This application is directed to systems and methods for monitoring a patient, and in particular, to systems and methods for determining a hemodynamic parameter of a patient

BACKGROUND

Traditional non-invasive blood pressure monitoring devices operate by inflating a blood pressure cuff to a pressure above a patient's systolic blood pressure. Because the systolic pressure is usually not known prior to inflation, the cuff must be inflated to such a pressure to ensure that the patient's arterial blood flow is completely occluded. Once above systole, pressure data collected during inflation and/or deflation of the cuff is used to determine, for example, systolic and diastolic pressures of the patient.

Many physicians are used to taking blood pressure readings using manual blood pressure devices, such as sphygmomanometers. Thus, due to their familiarity with manual devices, physicians have difficulty relying on measurements taken by automated blood pressure devices, even though automated devices are relatively common. On the other hand, blood pressure data collected using manual blood pressure devices are prone to inaccuracy. For instance, when taking measurements using such devices, physicians typically listen for Korotkoff sounds, and look up to view a pressure gauge associated with such devices once these sounds are heard. However, the lag between hearing such sounds and viewing the pressure gauge causes inaccuracy in each respective reading.

The systems and methods described herein are directed toward overcoming the difficulties described above.

SUMMARY

In an exemplary embodiment of the present disclosure, a system for monitoring a patient includes a sensor configured to determine a first characteristic and a second characteristic of an at least partially occluded artery. The system also includes a control module in communication with the sensor and configured to determine a hemodynamic parameter of the patient based on the first and second characteristics. The control module is operable in an automatic operating mode and a manual operating mode. The automatic operating mode is characterized by the sensor determining, in response to one or more sensor control signals automatically generated by the control module, the first and second characteristics during at least one of automatic inflation and automatic deflation of a cuff associated with the control module. The manual operating mode is characterized by the sensor determining, in response to manual actuation of a trigger associated with the sensor, the first and second characteristics during at least one of inflation and deflation of the cuff.

In another exemplary embodiment of the present disclosure, a method of determining a hemodynamic parameter of a patient includes selecting a first operating mode associated with a control module of a patient monitoring system, the system including a sensor in communication with the control module, and a trigger in communication with the sensor. The method also includes substantially occluding an artery of the patient while the system is under automatic control of the control module in the first operating mode, and determining, with the sensor and in response to one or more sensor control signals automatically generated by the control module, a first characteristic and a second characteristic associated with the artery while in the first operating mode. The method also includes selecting a second operating mode associated with the control module and substantially occluding the artery of the patient while in the second operating mode. The method further includes determining, with the sensor and in response to manual actuation of the trigger, a third characteristic and a fourth characteristic associated with the artery while in the second operating mode. The method also includes determining, with the control module, the hemodynamic parameter of the patient based on at least one of the first characteristic, the second characteristic, the third characteristic, and the fourth characteristic.

In still another exemplary embodiment of the present disclosure, a method of determining a hemodynamic parameter of a patient includes selecting a first operating mode associated with a control module of a patient monitoring system, the system including a sensor in communication with the control module, and a trigger in communication with at least one of the sensor and the control module. The method also includes automatically inflating a cuff to an occlusion pressure under the control of the control module in the first operating mode, wherein automatically inflating the cuff at least partially occludes an artery of the patient. The method further includes automatically deflating the cuff from the occlusion pressure to a deflated pressure less than the occlusion pressure under the control of the control module in the first operating mode. The method also includes determining, with the sensor and in the first operating mode, a first systolic pressure and a first diastolic pressure associated with the artery, and displaying the first systolic and first diastolic pressures via a communication module in communication with the control module. The method further includes selecting a second operating mode associated with the patient monitoring system and manually inflating the cuff to the occlusion pressure in the second operating mode, wherein manually inflating the cuff at least partially occludes the artery. The method also includes manually deflating the cuff from the occlusion pressure to the deflated pressure in the second operating mode, and determining, with the sensor and in response to manual actuation of the trigger in the second operating mode, a second systolic pressure and a second diastolic pressure associated with the artery. The method further includes displaying the second systolic and second diastolic pressures via the communication module.

DETAILED DESCRIPTION

Figure 1:
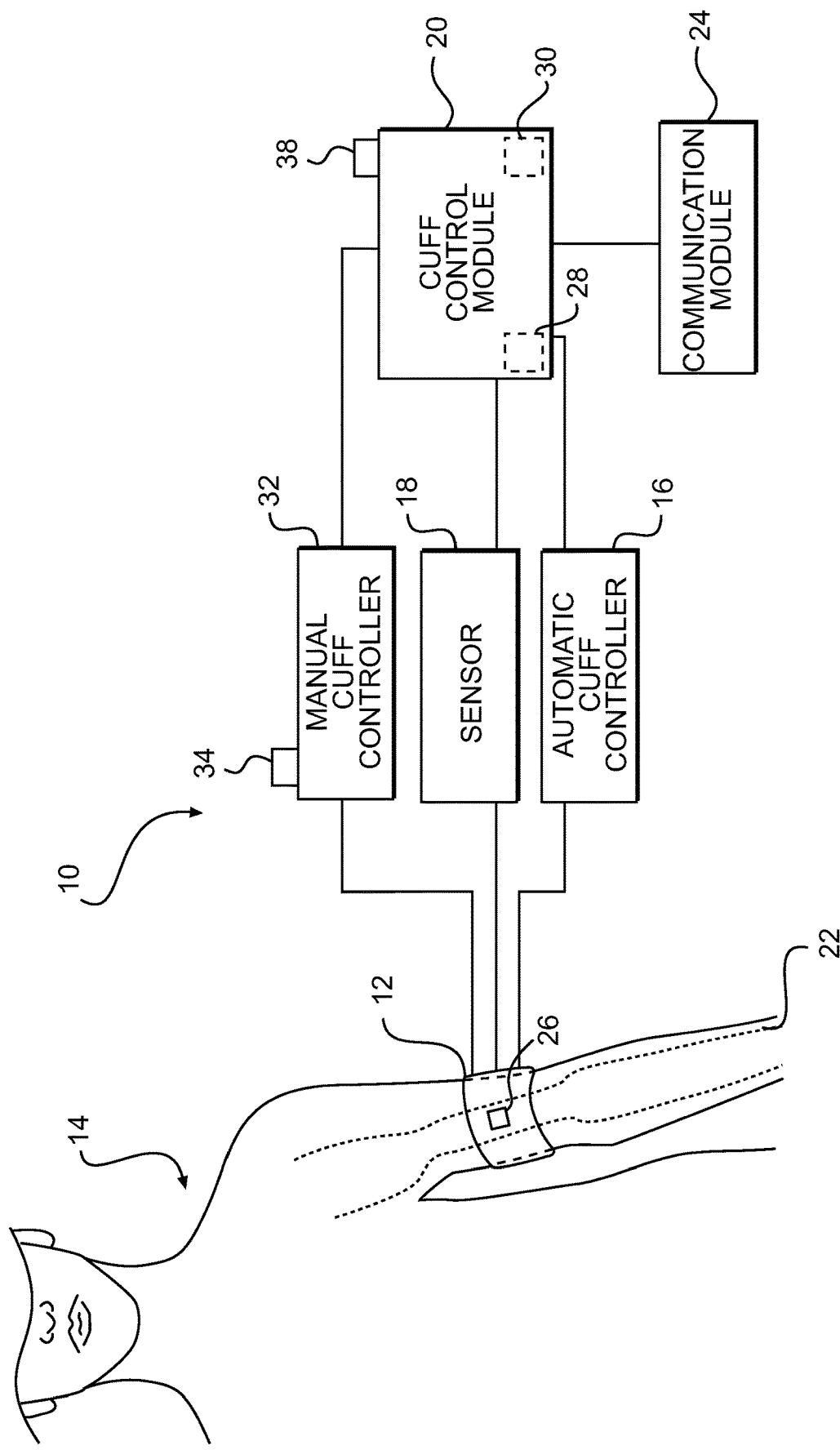
FIG. 1 illustrates a system according to an exemplary embodiment of the present disclosure.

FIG. 1 illustrates a monitoring system 10 according to an exemplary embodiment of the present disclosure. System 10 can be configured to monitor a patient 14, and in some embodiments, to determine a hemodynamic parameter of the patient 14. System 10 can include a cuff 12 configured to at least to partially occlude the movement of blood through a vessel, vein, and/or artery 22 of the patient 14. In some embodiments, cuff 12 can be configured to completely occlude an artery 22 of patient 14, and the artery 22 may be, for example, the brachial artery. For example, the cuff 12 may be inflated to any known occlusion pressure, and at such an occlusion pressure, the artery 22 may be at least partially occluded. The cuff 12 may also be deflated to a deflated pressure below (i.e., less than) the occlusion pressure, and at such a pressure, the artery 22 may be substantially unoccluded. Although shown in FIG. 1 as surrounding the upper arm of patient 14, cuff 12 may be adapted for placement on any suitable portion of the patient's body, including, for example, a wrist, a finger, an upper thigh, or an ankle. In addition, one or more cuffs 12 could be placed at different locations about and/or on patient 14 for use with system 10.

The exemplary cuffs 12 of the present disclosure may be formed from any medically approved material known in the art. Such materials may be highly flexible, durable, and suitable for contact with, for example, the skin of the patient 14. Such materials may also be tear-resistant, fluid-impermeable, and recyclable. Such materials may include, for example, paper, cloth, mesh and/or polymers such as polypropylene or polyethylene. In still further exemplary embodiments, such materials may be coated and/or otherwise treated with one or more additives that cause the material to become biodegradable within a desired time interval (e.g., within 2 to 3 months). Each of the exemplary cuffs 12 described herein may have a respective length, width, and inflated height suitable for use with a particular patient 14. For example, a first cuff 12 intended to be used with an adolescent patient 14 may have a first deflated length and a first deflated width, and a second cuff 12 intended for use with an adult patient 14 may have a corresponding second deflated length and second deflated width. In such an exemplary embodiment, the first deflated length may be less than the second deflated length and the first deflated width may be less than the second deflated width. In exemplary embodiments, inflated lengths and widths of the exemplary cuffs described herein may be different than the corresponding deflated lengths and widths.

The cuff 12 may include one or more bladders (not shown) or other like inflatable devices. Such a bladder may be formed from a single piece of material or, alternatively, from two or more pieces of material that are joined together through heat sealing, ultrasonic or RF welding, adhering, and/or other like processes. In still further exemplary embodiments, the cuff 12 may form one or more inflatable pockets that perform the same functions as a bladder. In such exemplary embodiments, the bladder may be omitted. It is understood that the cuff 12 and/or bladder may be inflatable to an occlusion pressure of approximately 160 mm Hg or greater to assist in at least partially occluding the artery 22. In exemplary embodiments, the cuff 12 may include one or more ports (not shown) fluidly connected to the internal pocket or bladder to assist with inflation and/or deflation thereof.

The pressure or volume of fluid within cuff 12 may be controlled by one or more cuff controllers fluidly connected and/or otherwise operably associated with the cuff 12. For example, the system 10 may include an automatic cuff controller 16 and a manual cuff controller 32, and both cuff controllers 16, 32 may be fluidly connected to cuff 12 for inflation and/or deflation thereof. In exemplary embodiments, one or both cuff controllers 16, 32 may be releasably and/or otherwise removably fluidly connected to cuff 12 via separate respective ports. In such an embodiment, both cuff controllers 16, 32 may be fluidly connected to cuff 12 simultaneously (i.e., at the same time). Alternatively, cuff 12 may include a single connection port by which cuff controllers 16, 32 may be separately connected thereto. In still further embodiments, one or both cuff controllers 16, 32 may be permanently connected to cuff 12. In such embodiments, a tube, hose, or other like fluid channel may be integrally connected with, for example, the bladder of cuff 12.

Automatic cuff controller 16 can include a pump or similar device configured to inflate and/or deflate the cuff 12. For example, automatic cuff controller 16 could supply cuff 12 with a fluid such as air to increase the pressure or volume within cuff 12. In other embodiments, cuff controller 16 could include mechanical, electrical, or chemical devices configured to control occlusion of artery 22 via cuff 12. Automatic cuff controller 16 may be mechanically, fluidly, and/or operably connectable to one or more of the ports described herein to assist in inflating and/or deflating cuff 12. Automatic cuff controller 16 may also be operatively connected and/or otherwise in communication with a cuff control module 20 of system 10. In such embodiments, automatic cuff controller 16 may be configured to selectively inflate and deflate the cuff 12 in response to one or more control signals received from the cuff control module 20. Cuff control module 20 will be described in greater detail below.

In some embodiments, automatic cuff controller 16 can generally maintain cuff 12 at about a target or reference pressure. For example, once a target or reference pressure has been chosen, automatic cuff controller 16 could inflate and maintain cuff 12 to the target or reference pressure. While the present disclosure refers to a target or reference pressure, it should be understood that the actual pressure applied by cuff 12 may vary slightly from the target or reference. For example, the actual pressure applied to patient 14 may generally remain within appropriate limits, such as, for example, within 2%, 5%, 10%, or 20% of the target or reference pressure. This difference between the chosen target or reference pressure and the actual pressure applied by cuff 12 may be caused by the occlusion efficiency of the respective cuff 12. A cuff's "occlusion efficiency" may be defined as the ease or difficulty with which air pressure within the cuff 12 is transferred to force on the underlying artery 22. For example, cuffs 12 having a higher occlusion efficiency may be capable of applying a relatively greater force to such an artery 22 at a given inflation pressure than a like cuff 12 having a relatively lower occlusion efficiency.

Manual cuff controller 32 may also be configured to selectively inflate and deflate cuff 12, and to thereby substantially occlude and unocclude artery 22, in ways similar to automatic cuff controller 16. However, manual cuff controller 32 may be hand and/or otherwise manually operated by a user of system 10 to inflate and deflate cuff 12. Manual cuff controller 32 may comprise any manually-operated device configured to supply fluid to and release fluid from cuff 12. In exemplary embodiments, manual cuff controller 32 may comprise a manually operated bulb, pump, or other like device commonly associated with conventional manual sphygmomanometers. In such embodiments, manual cuff controller 32 may also include one or more valves (not shown) or other like flow control devices configured to maintain fluid, such as air, within cuff 12 during inflation thereof, and to facilitate the gradual release of such fluid from cuff 12 during deflation. The valve may be manually controlled by the user to regulate the flow of air into and out of cuff 12 during, for example, auscultation. In exemplary embodiments, the valve may comprise a manually controlled check valve or other like device.

In exemplary embodiments, manual cuff controller 32 may include one or more triggers 34 depressible by a user of manual cuff controller 32 during auscultation or other like patient monitoring activities. Trigger 34 may comprise one or more buttons, switches, knobs, or other like actuatable components of manual cuff controller 32, and a trigger 34 of the present disclosure may be in communication with and/or otherwise operably connected to cuff control module 20. Trigger 34 may be directly connected to cuff control module 20 and/or may be connected thereto via manual cuff controller 32. In such embodiments, a user may depress, turn, manipulate, and/or otherwise actuate trigger 34 during auscultation and upon hearing or determining an event. For example, a user may actuate trigger 34 upon hearing Korotkoff sounds associated with a systolic pressure and a diastolic pressure of patient 14. When trigger 34 is actuated in this way, trigger 34 and/or manual cuff controller 32 may generate one or more signals indicative of such an event, and such signals may be directed to cuff control module 20 and/or other components of system 10. In exemplary embodiments, trigger 34 may be associated with the valve discussed above. In particular, in such embodiments, manual cuff controller 32 may include a valve having a trigger 34. Such a valve may be configured to release air from cuff 12 and, upon hearing Korotkoff sounds associated with a systolic pressure and/or a diastolic pressure of patient 14, a user of manual cuff controller 32 may actuate the trigger 34 associated with such a valve to indicate that such sounds have been heard.

System 10 can further include a sensor 18 configured to receive a signal associated with patient 14, automatic cuff controller 16, manual cuff controller 32, and/or cuff control module 20. In each of the exemplary embodiments described herein, sensor 18 may determine one or more characteristics associated with artery 22 of patient 14. Such characteristics may include, for example, a systolic pressure, a diastolic pressure, a mean arterial pressure, and/or other known characteristics associated with cuff 12, artery 22, and/or patient 14. In further exemplary embodiments sensor 18 may be configured to determine one or more of an oscillation signal strength, an ambient temperature, a humidity, a cumulative cycle count of cuff 12, a volume of cuff 12, an occlusion pressure of cuff 12, a cumulative time associated with cuff 12 being inflated to a reference volume and/or pressure, and/or other like characteristics. In exemplary embodiments, the reference pressure may be approximately 100 mm Hg, and the target pressure may be equal to the reference pressure. The reference volume may be any volume of cuff 12 and/or the bladder associated with reaching such a reference pressure. The sensor 18 may comprise devices including, but not limited to, one or more of a pressure sensor, a thermometer, a thermocouple, a hygrometer, and/or a timer. The sensor 18 may be located at positions including, but not limited to, within, on, or about cuff 12. System 10 may further include a plurality of sensors 18, and may include a high-resolution sensor or pneumatic sensor designed to operate in conjunction with cuff 12.

In some embodiments, sensor 18 can be configured to receive a signal associated with an at least partially occluded artery 22 of patient 14. Such an input signal can arise from blood movement through a partially occluded artery 22 or from a signal associated with an occluded blood vessel. Sensor 18 could sample various aspects or characteristics of artery 22 multiple times at various intervals. In additional exemplary embodiments, sensor 18 could provide an indication of blood vessel movement, such as, for example, oscillations arising from vascular expansion or contraction. Such oscillations may produce a signal that is detected by sensor 18, and the strength of such an oscillation signal may be used to determine a hemodynamic parameter of the patient 14. For example, sensor 18 could be configured to detect an occlusion pressure or volume of cuff 12 that may vary periodically with the cyclic expansion and contraction of the artery 22 of patient 14.

In additional exemplary embodiments, sensor 18 may be configured to read, scan, sense, detect, and/or otherwise input information associated with cuff 12. Such information may include, for example, an occlusion efficiency that is particular to the actual cuff 12 being used, or an occlusion efficiency associated with the type, size, design, model, and/or style of cuff 12 being used. It is understood that the type, size, design, model, and/or style of cuff 12 may be characteristics that are unique or particular to the actual cuff 12 being used. For example, such characteristics may include and/or may be indicative of the length, width, inflated height, and/or other dimensions of the cuff 12, the shape of cuff 12, the number of bladders included in cuff 12, the length, width, and/or inflated height of such bladders, the maximum inflated volume of cuff 12, materials used to construct cuff 12, and whether cuff 12 is intended for use with a child, adolescent, adult, elderly, and/or bariatric patient 14, among other things. In such exemplary embodiments, sensor 18 may comprise an RFID reader, a barcode reader, an MICR reader, a conductance sensor, a resistance sensor, a magnetic sensor, and/or any other like reading device known in the art.

Such a sensor 18 may be configured to sense, scan, detect, and/or otherwise read information carried by one or more information features 26 associated with cuff 12. In addition to standard text, such information features 26 may comprise one of an RFID tag, a barcode, MICR printing, a conductive, resistive, and/or magnetic strip of material, and/or other known means for providing information. For example, such information features 26 may communicate an occlusion efficiency of cuff 12 to the sensor 18 and/or to a user of the system 10. Such information features 26 may also communicate an identification parameter particular to cuff 12. Such an identification parameter may be indicative of, for example, the type, size, design, model, and/or style of cuff 12 being used. Such an identification parameter may also comprise, for example, a serial number, a model number, a part number, and/or any other like information enabling the particular cuff 12 to be identified for purposes of tracking or recording, for example, a cumulative cycle count, an age of the cuff, and/or any of the other characteristics described herein. One or more such information features 26 may be disposed on an outer exposed surface of cuff 12 for reading by sensor 18 or, alternatively, may be embedded within and/or formed integrally with cuff 12. Alternatively, in further embodiments, such information features 26 may be omitted.

Sensor 18 can further be configured to generate one or more output signals indicative of each respective characteristic that is determined. The output signal may be generated based on and/or otherwise in response to an input signal received from patient 14. In further embodiments, the output signal generated by sensor 18 may be generated in response to activation of trigger 34, in response to a control signal received from automatic cuff controller 16, and/or in response to a control signal received from cuff control module 20. For example, sensor 18 may be configured to, in response to activation of trigger 34, determine a characteristic associated with an at least partially occluded artery 22, and to generate an output signal indicative of the characteristic. Sensor 18 may also be configured to, in response to a control signal received from cuff control module 20, determine a characteristic associated with an at least partially occluded artery 22, and to generate an output signal indicative of the characteristic.

One or more of the characteristics determined by sensor 18 may be used to determine one or more hemodynamic parameters of patient 14. As described herein, a hemodynamic parameter can include any indication of cardiac or vascular health, such as, for example, an indication of cardiac, circulatory, or vascular functionality. Specifically, a hemodynamic parameter can include a heart rate, a blood pressure, a vessel compliance, an aortic index, an augmentation index, a reflected wave ratio, and/or an indication of treatment. Such a blood pressure can include systolic pressure, diastolic pressure, and/or mean arterial pressure, and vessel compliance may include, for example, arterial stiffness. An indication of treatment can include a parameter reflecting the effect of a drug treatment, or one or more treatments of a disease state. It is understand that a hemodynamic parameter may comprise one or more characteristics the artery 22 and vice versa. Accordingly, in exemplary embodiments, and as described herein, the terms "hemodynamic parameter" and "characteristic" may be used interchangeably where applicable.

In some embodiments, a hemodynamic parameter can be determined based on a suprasystolic measurement. In other embodiments, a hemodynamic parameter can be determined based on a first set of data obtained during inflation of cuff 12 and a second set of data obtained during general maintenance of cuff 12 at about a target or reference pressure. Such a target or reference pressure may be, for example, an occlusion pressure wherein the artery 22 is at least partially occluded. The first or second sets of data can include various data associated with a signal waveform associated with patient 14 and/or cuff 12, and may include oscillation signal strength, amplitude, frequency, morphology, feature, or mathematically derived data. Data may be derived from a derivative, integration, or frequency analysis, such as, for example, a fast-Fourier transform. Data may also be derived from various algorithms, including curve fitting, a neural network, filtering, smoothing, or data processing. It is understood that the system 10 may comprise any known oscillometric or auscultation system, and that the system 10 may be configured to perform and/or otherwise employ any known oscillometric or auscultation methods.

As noted above, cuff 12, cuff controllers 16, 32, and sensor 18 may be operably associated with a cuff control module 20. In exemplary embodiments, cuff control module 20 could include one or more processors 28 configured to control one or more operations of cuff 12, cuff controller 16, and/or sensor 18. For example, cuff control module 20 can control programmed and/or otherwise automatic inflation and/or deflation of cuff 12 via control of cuff controller 16. Cuff control module 20 and/or one or more processor 28 associated therewith may be configured to, for example, receive the output signals generated by sensor 18 and/or trigger 34. Cuff control module 20 and/or processor 28 may be configured to determine a hemodynamic parameter of patient 14 based on, for example, the one or more output signals of sensor 18. As described above, one or more such signals may be generated by sensor 18 in response to actuation of trigger 34. One or more such signals may also be generated by sensor 18 in response to control signals received from cuff control module 20 and/or automatic cuff controller 16.

In some embodiments, cuff control module 20 may control inflation of cuff 12 to the occlusion pressure described herein, and may maintain inflation of cuff 12 at about the occlusion pressure for a predetermined period of time. For example, cuff control module 20 could control inflation of cuff 12 to a calculated, selected, or predetermined occlusion pressure. Cuff control module 20 could then generally maintain cuff 12 at about the occlusion pressure for a defined time period, such as, for example, less than about 10 seconds. Cuff control module 20 may then control deflation of cuff 12 while directing sensor 18 to determine one or more characteristics of artery 22. In other embodiments, the occlusion pressure could be generally maintained for a defined number of cycles, such as, for example, six, eight, or ten cycles, and cuff control module 20 may pause such automatic inflation and deflation of cuff 12 for a predetermined time interval between cycles. Information obtained by sensor 18 during such cycles may be used to determine, for example, a mean blood pressure, a heart rate, an arterial stiffness, or other like hemodynamic parameters of patient 14.

In an exemplary embodiment, cuff control module 20 and/or processor 28 may include a signal analysis module 30 configured to analyze one or more signals received from sensor 18 and/or other inputs. For example, signal analysis module 30 can include one or more filters configured to filter a signal associated with sensor 18 or cuff control module 20. Such filters can include band-pass, high-pass, or low-pass filters. In such exemplary embodiments, signal analysis module 30 may assist in determining the hemodynamic parameter of the patient 14.

Cuff control module 20 may also include a mode selector 38 operably connected to processor 28 and/or signal analysis module 30. Mode selector 38 may comprise any known knob, switch, dial, button, or other like input device configured to enable a user of system 10 to select between one or more operating modes of system 10. For example, mode selector 38 may enable a user to select between an automatic operating mode in which sensor 18 determines a characteristic of artery 22 in response to a cuff control signal generated by and/or received from cuff control module 20, and a manual operating mode in which sensor 18 determines a characteristic of artery 22 in response to manual actuation of trigger 34. In exemplary embodiments, the automatic operating mode may be characterized by substantially fully-automatic operation of system 10. For example, in such an operating mode, the user may enter, program, and/or otherwise select one or more parameters of operation, and system 10 may automatically determine one or more characteristics associated artery 22 based on the selected parameters. Such parameters may include, for example, at least one of a rate of inflation of cuff 12, a rate of deflation of cuff 12, a quantity of artery occlusion cycles, and a time interval between cycles.

In further exemplary embodiments, the manual operating mode may be characterized by substantially fully-manual operation of system 10. For example, in such an operating mode, the user may manually inflate cuff 12 using manual cuff controller 32, may utilize a stethoscope or other like device to observe Korotkoff sounds associated with artery 22, and may manually actuate trigger 34 upon hearing such sounds. The user may also manually control the rate of inflation and/or deflation of cuff 12 using the valve associated with trigger 34. Alternatively, in exemplary embodiments of the manual operating mode, the user may utilize automatic cuff controller 16 to aid in inflation and/or deflation of cuff 12. For example, while in a manual operating mode, one of inflation and deflation of cuff 12 may be performed automatically in response to one or more cuff control signals generated by cuff control module 20, and the other of inflation and deflation of cuff 12 may be performed manually using manual cuff controller 32. Such an exemplary manual operating mode may be helpful for users with arthritis, carpal tunnel syndrome, or other ailments hindering the user's ability to manually inflate and/or deflate cuff 12 using manual cuff controller 32.

In still further exemplary embodiments, mode selector 38 may enable a user to select between the automatic operating mode, the manual operating mode, and a hybrid operating mode. Such a hybrid operating mode may be substantially similar to the exemplary manual operating mode described above in which one of inflation and deflation of cuff 12 may be performed automatically in response to one or more cuff control signals generated by cuff control module 20, and the other of inflation and deflation of cuff 12 may be performed manually. In an exemplary hybrid operating mode, both manual cuff controller 32 and automatic cuff controller 16 may be enabled to inflate and/or deflate cuff 12, thereby substantially occluding and substantially unoccluding artery 22. In such a hybrid operating mode, for example, system 10 may control automatic cuff controller 16 to automatically inflate and deflate for one or more cycles. During such control, sensor 18 may make one or a series of automatic characteristic determinations associated with artery 22. Once such cycles are complete, and while cuff control module 20 is in the hybrid operating mode, a user may manually inflate and deflate cuff 12 using manual cuff controller 32. As noted above, sensor 18 may also be used to determine characteristics of artery 22 during such manual inflation and deflation of cuff 12.

Cuff control module 20 may further include any type of memory (not shown) known in the art. For example, such memory may comprise random access memory (RAM), read-only memory (ROM), or other types of memory configured to store information associated with the characteristics determined by sensor 18. For example, such memory may be configured to store a plurality of sensed characteristics for later use by processor 28. Memory of cuff control module 20 may also be configured to store one or more control algorithms associated with system 10. Such control algorithms may be used by cuff control module 20 to, for example, control operation of automatic cuff controller 16 during one or more of the manual, automatic, and/or hybrid operating modes described herein. Such algorithms may also be used by, for example, processor 28 to determine one or more hemodynamic parameters of patient 14. For example, information carried by the output signals generated by sensor 18 may be used as inputs to such algorithms. Processor 28 may, thus, utilize such algorithms to determine one or more hemodynamic parameters of patient 14 based on one or more such inputs.

As shown in FIG. 1, system 10 can further include a communication module 24 configured to provide communication to patient 14 or one or more users of system 10. For example, communication module 24 could include a monitor, a digital read-out, an analog gauge, dial, or read-out, an LCD screen, or other known device configured to display and/or otherwise output one or more hemodynamic parameters and/or one or more determined characteristics. In other embodiments, communication module 24 could include a wired, wireless, RF, or other known transmitter configured to transmit data to a remote location. Communication module 24 may further include audio output to communicate with patient 14 and/or a user of system 10.

Figure 2:
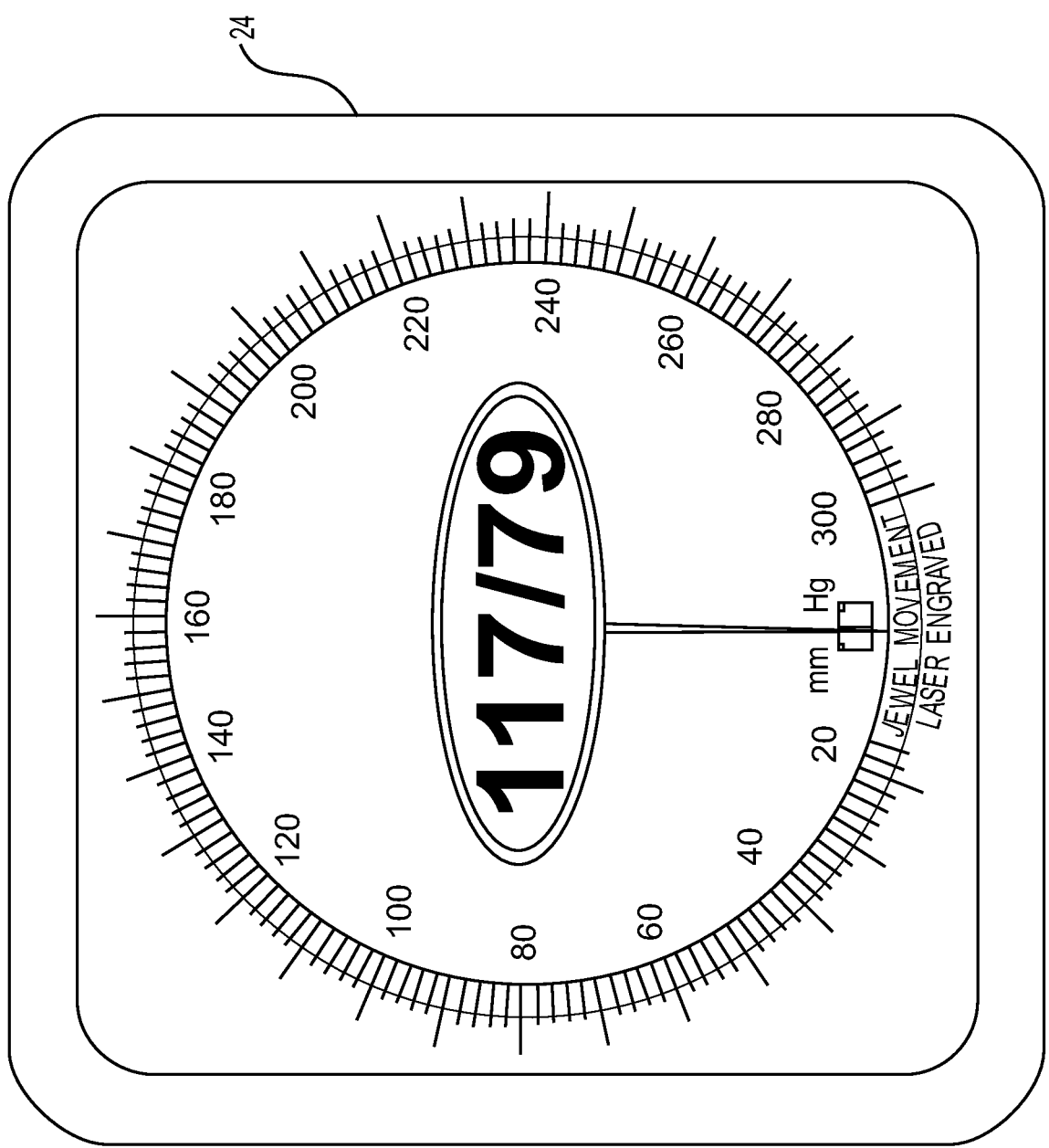
FIG. 2 illustrates a module associated with the system of FIG. 1.
Figure 3:
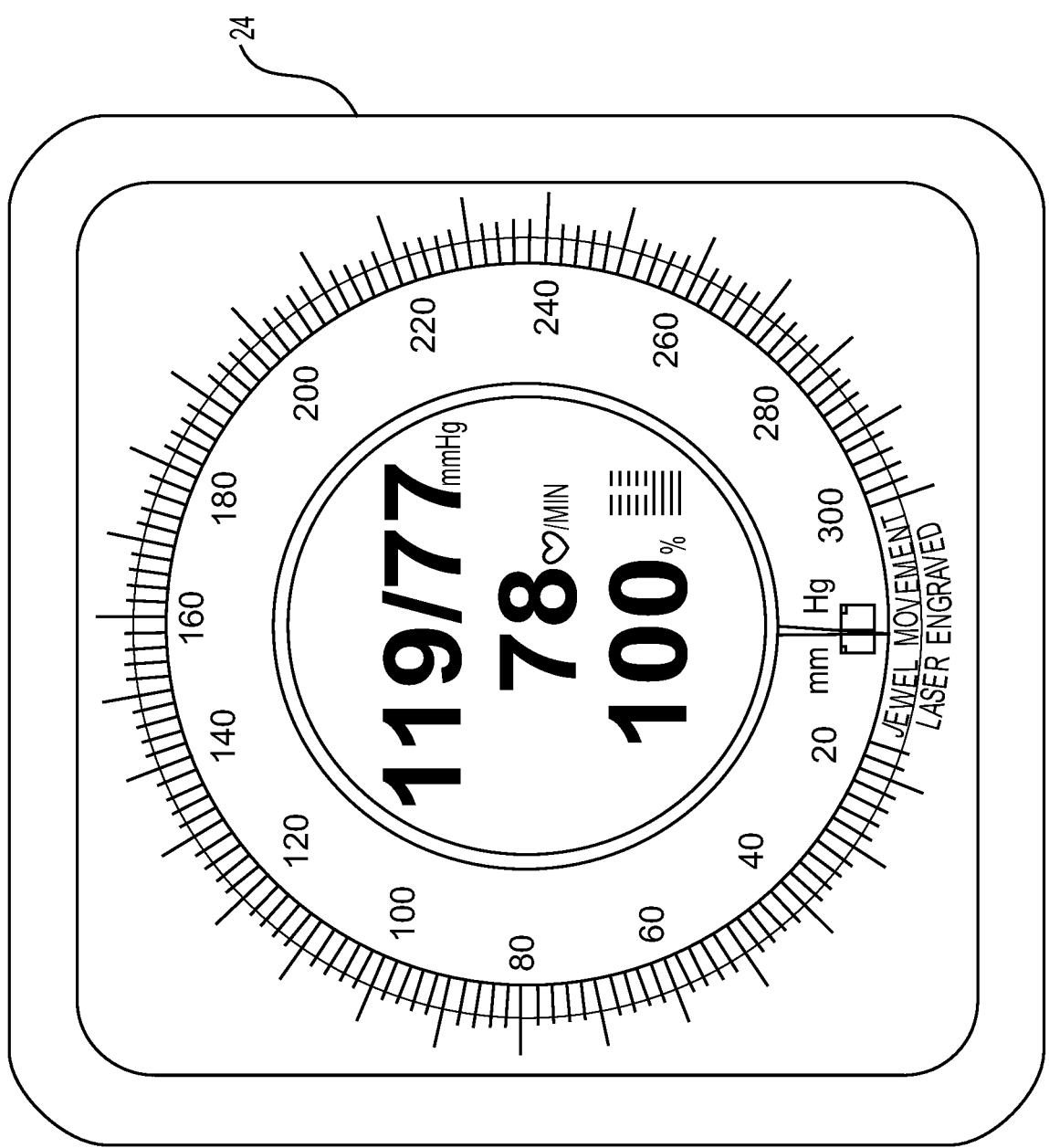
FIG. 3 illustrates another embodiment of a module associated with the system of FIG. 1.
Figure 4:
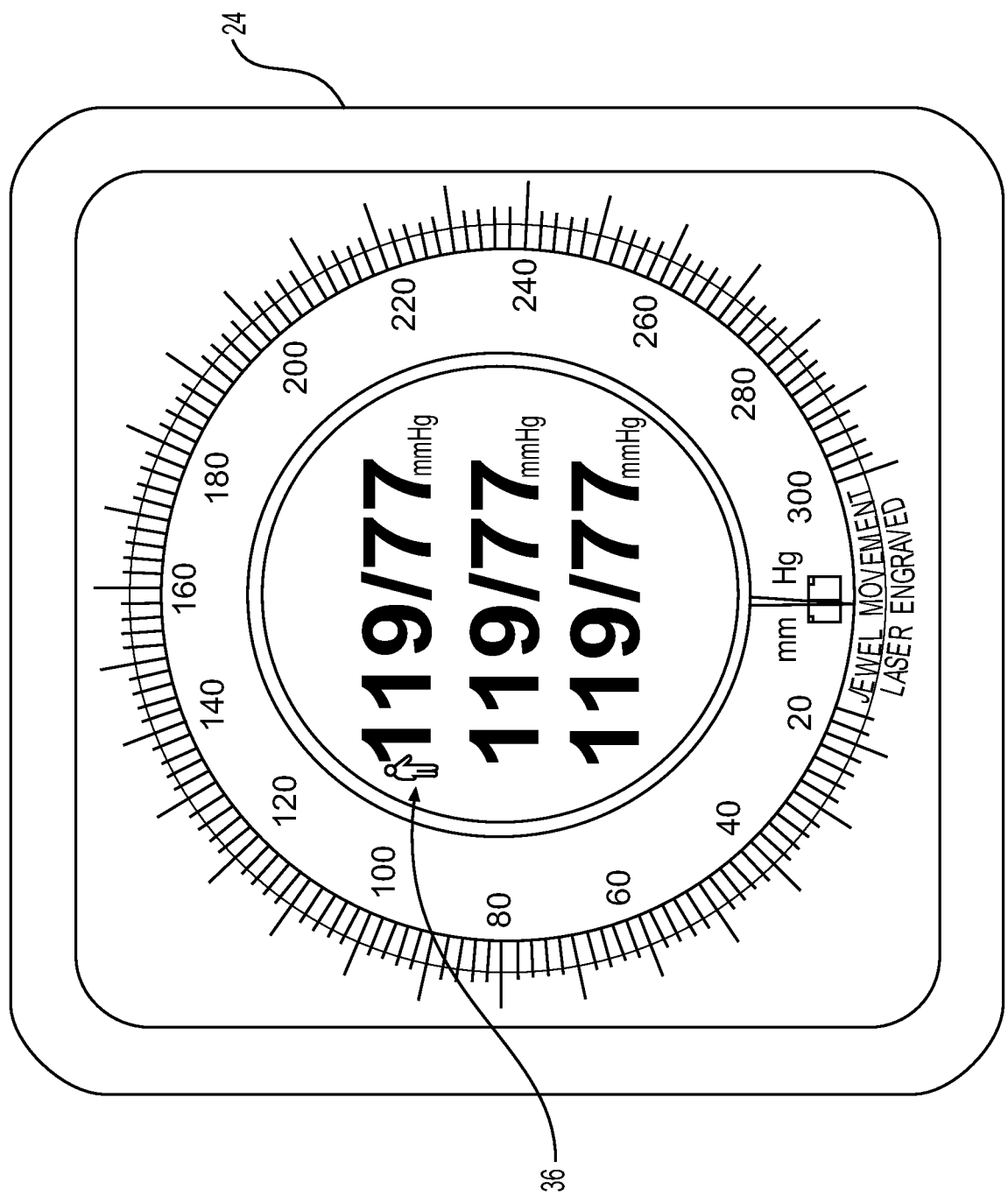
FIG. 4 illustrates a further embodiment of a module associated with the system of FIG. 1.

FIGS. 2-4 illustrate exemplary communication modules 24 of the present disclosure. The configurations of communication modules 24 illustrated in FIGS. 2-4 are merely exemplary, and in further embodiments, more, less, or different information may be displayed and/or otherwise outputted by communication module 24 than that shown in FIGS. 2-4. As shown in FIGS. 2-4, an exemplary communication module 24 may include an analog dial, a digital dial, and/or other indicator of blood pressure, as measured in millimeters of mercury (mmHg) or other known units. In such embodiments, communication module 24 may comprise a mercury, jewel, or manual manometer. Communication module 24 may also include a digital or other like display such that one or more characteristics determined by sensor 18 may be displayed and/or otherwise outputted thereby. For example, as shown in FIG. 2, such a digital display may output a systolic blood pressure and a diastolic blood pressure. Such characteristics may be displayed contemporaneously with a corresponding measurement and/or other determination made by sensor 18. Additionally, in one or more of the operating modes described herein, such characteristics may be displayed contemporaneously with a corresponding determination made by sensor 18, and may remain displayed by communication module 24 while a manual determination of blood pressure is made using sensor 18 and/or manual cuff controller 32. In such a configuration, a user of system 10, such as a physician, may be able to easily compare an automatic blood pressure determination with a corresponding manual blood pressure determination. In such configurations, the various determined characteristics may be outputted simultaneously (i.e., at the same time) by communication module 24 for comparison purposes. It is understood that such simultaneous output by communication module 24 may include displaying a first characteristic, and then displaying a second characteristic, determined later in time, while the first characteristic is displayed.

As shown in FIG. 3, communication module 24 may be configured to simultaneously display information indicative of more than one type of determined characteristic. For example, communication module 24 may be configured to display information indicative of blood pressure, heart rate (beats per minute), pulse oxidation (percentage), or other like characteristics determined by sensor 18. In exemplary embodiments, such information may be displayed substantially continuously in applications in which system 10 is used to continuously monitor patient 14.

Additionally, as shown in FIG. 4, communication module 24 may be configured to simultaneously display information indicative of characteristics obtained through multiple readings, measurements, or other determinations. For example, communication module 24 may be configured to display information indicative of a plurality of blood pressures, or other like characteristics, determined by sensor 18 over a series of measurement cycles. Such information displayed by communication module 24 may be determined by sensor 18 as cuff 12 is automatically inflated and/or deflated by automatic cuff controller 16 during the various operating modes described herein. Additionally, communication module 24 may simultaneously display information indicative of one or more blood pressures or other like characteristics determined by sensor 18 as cuff 12 is manually inflated and/or deflated by manual cuff controller 32 during the various operating modes described herein.

Communication module 24 may also display an icon or other like indicator 36 associated with characteristics determined during such operating modes. Such a visual indicator 36 may enable a user of system 10 to determine, for example, which of the displayed information, characteristics, and/or parameters was obtained during manual operation and which was determined during automatic operation. For example, communication module 24 may display such an indicator 36 adjacent information associated with characteristics determined during manual operation of manual cuff controller 32, such as during a manual operating mode. By displaying indicator 36 adjacent such characteristics, a user may easily distinguish such manually determined characteristic from other simultaneously displayed characteristics determined automatically.

In further embodiments, communication module 24 may also display one or more hemodynamic parameters determined based on the characteristics described herein. For example, cuff control module 20 may be configured to determine an average blood pressure of patient 14 based on automatically and manually determined blood pressures, and communication module 24 may be configured to display such an average blood pressure or other like hemodynamic parameters simultaneously with any of the information or characteristics described herein.

In addition to the components outlined above, system 10 may include various other components as required, such as, for example, a power source and a user input device. One or more components described herein may be combined or may be separate and operate with wireless or wired communication links. Moreover, the various components of system 10 could be integrated into a single unit or assembly, or may operate as separate units or assemblies. For example, the cuff control module 20, automatic cuff controller 16, processor 28, sensor 18, communication module 24, and/or signal analysis module 30 described herein may be disposed within a single housing, and such a housing may be configured for handheld use. In such exemplary embodiments, manual cuff controller 32 and/or automatic cuff controller 16 may be removably attachable to such a housing. Alternatively, manual cuff controller 32 and/or automatic cuff controller 16 may be permanently and/or integrally connected to such a housing.

Figure 5:
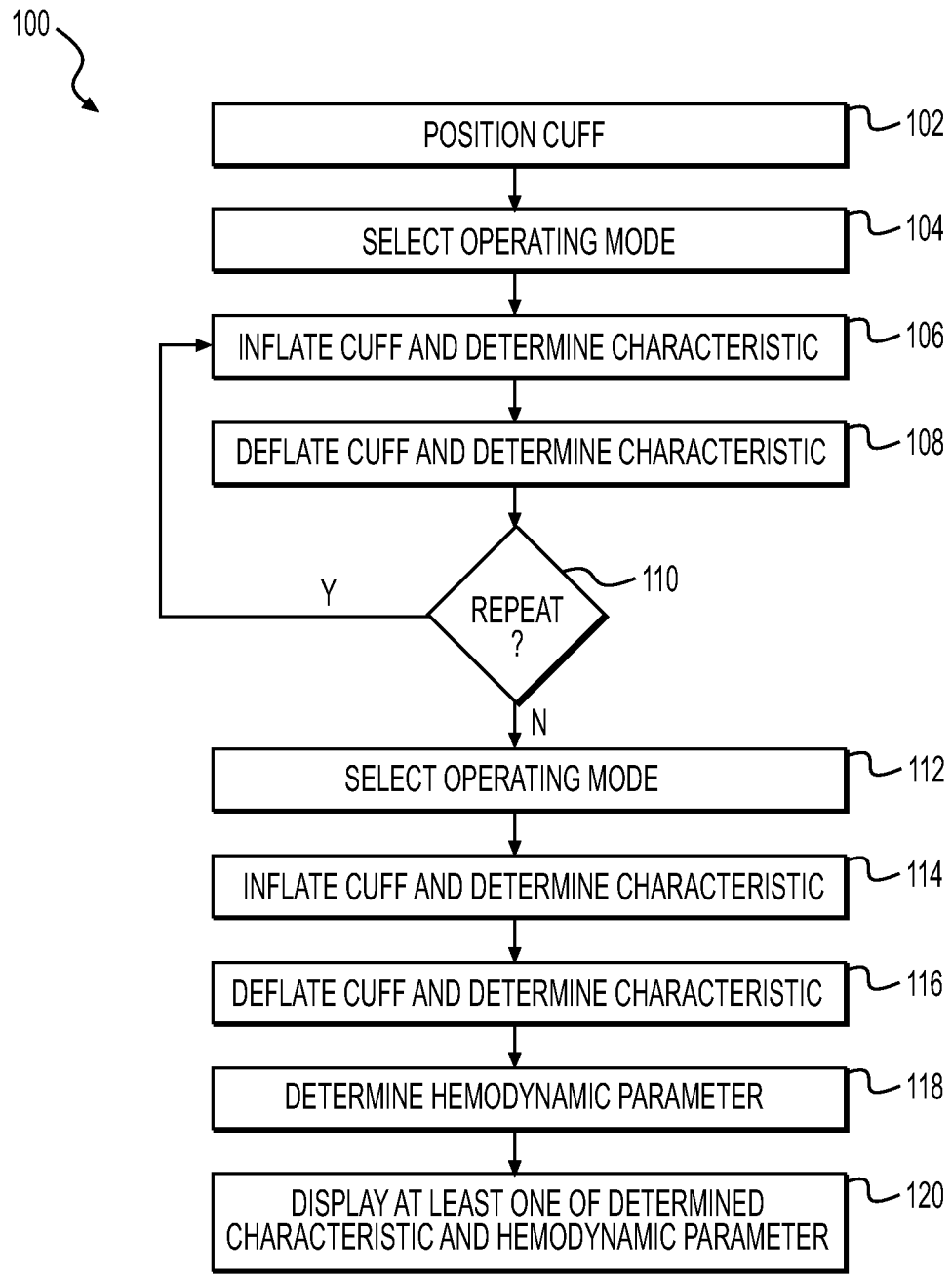
FIG. 5 illustrates a flow chart showing an exemplary method of the present disclosure.

As shown in the exemplary flow chart 100 illustrated in FIG. 5, methods of monitoring patient 14 and/or determining a hemodynamic parameter of patient 14 may include determining one or more characteristics associated with patient 14 and, in particular, one or more characteristics of artery 22. Such methods may comprise oscillometric methods, auscultation methods, and/or any other known patient monitoring methods. For example, such methods may include positioning cuff 12 about a limb of patient 14 (Step: 102). In exemplary embodiments, a substantially deflated cuff 12 may be positioned around a portion of an arm of patient 14, such as above the elbow (i.e., circumferentially around the bicep and tricep). It is understood that in exemplary embodiments in which one or both of automatic cuff controller 16 and manual cuff controller 32 are removably attachable to, for example, cuff control module 20, Step: 102 may further include connecting one or both of such components to cuff control module 20.

Once cuff 12 is properly positioned, the user may (if not previously or integrally connected) fluidly connect one or both of automatic cuff controller 16 and manual cuff controller 32 to cuff 12. The user may also select an operating mode of system 10 (Step: 104) using mode selector 38 of cuff control module 20. For example, during examination of patient 14 prior to the arrival of a physician, a nurse or other healthcare professional may select either the automatic operating mode or the hybrid operating mode discussed herein.

Control may then proceed to Step: 106 where cuff control module 20 may direct and/or otherwise control automatic cuff controller 16 to inflate cuff 12 automatically and/or in accordance with a predetermined inflation protocol. Such an inflation protocol may comprise an algorithm, program, software, or routine stored in memory of cuff control module 20, and may be executed by processor 28. Additionally, in such an exemplary embodiment, the user may enter (i.e., select) various parameters of the automatic inflation protocol via communication module 24 and/or cuff control module 20. For example, upon selecting either the automatic operating mode, the manual operating mode, or the hybrid operating mode, the user may select one or more of a number of measurement cycles, an interval time between cycles, a cuff inflation rate, a cuff deflation rate, and/or a type or types of characteristics to be measured by sensor 18 during such measurement cycles. The user may select such parameters of the inflation protocol using a touch screen, a keyboard, a mouse, one or more buttons, or other like interface components (not shown) of communication module 24 and/or cuff control module 20.

Once such parameters have been selected, sensor 18 may determine the one or more desired characteristics under automatic control of cuff control module 20 (Step: 106). For example, sensor 18 may determine one or more characteristics associated with artery 22 while cuff 12 is substantially inflated and in response to control signals sent by cuff control module 20. It is understood that substantially inflating cuff 12 may substantially occlude artery 22 such that substantially no (i.e., negligible) blood may flow through artery 22. It is also understood that characteristics determined while artery 22 is in such a substantially occluded state may include a systolic blood pressure, and such a blood pressure may be determined by sensor 18 based on variations in the pressure within cuff 12. For example, cuff control module 20 may automatically inflate cuff 12 to an occlusion pressure that is greater than or equal to a systolic pressure of artery 22, and sensor 18 may measure and/or otherwise determine oscillations in cuff pressure according to one or more known oscillometric methods. Sensor 18 may generate signals indicative of the determined pressure oscillations and may direct such signals to cuff control module 20. Cuff control module 20 may utilize such information as inputs to one or more oscillometric pressure algorithms and may determine, for example, a systolic pressure associated with artery 22 based on such information.

At Step: 108, cuff control module 20 may control automatic cuff controller 16 to deflate cuff 12 automatically and/or in accordance with a predetermined deflation protocol similar to the inflation protocol described above. Additionally, at Step: 108 sensor 18 may determine one or more desired characteristics under automatic control of cuff control module 20. For example, sensor 18 may determine one or more characteristics associated with artery 22 while cuff 12 is substantially deflated and in response to control signals sent by cuff control module 20. In an exemplary embodiment, cuff control module 20 may automatically deflate cuff 12 to a deflated pressure less than the occlusion pressure, and at such a pressure, blood may resume flow through artery 22. At such a pressure, artery 22 may be in a substantially unoccluded state, and as described above with respect to Step: 106, sensor 18 may measure and/or otherwise determine oscillations in cuff pressure according to one or more known oscillometric methods. Sensor 18 may generate signals indicative of the determined pressure oscillations and may direct such signals to cuff control module 20. Cuff control module 20 may utilize such information as inputs to one or more oscillometric pressure algorithms and may determine, for example, a diastolic pressure associated with artery 22 based on such information. It is understood that any of the characteristics determined at Step: 106 and Step: 108 may be stored in memory of cuff control module 20, and may be displayed and/or otherwise outputted by communication module 24.

Control may then proceed to Step: 110 where cuff control module 20 may repeat steps Step: 106 and Step: 108 if more than one cycle of measurements was selected or requested by the user at Step: 104. If more than one automatic measurement cycle was requested by the user at Step: 104 (Step: 110—Yes), control may return to Step: 106 and the desired number of cycles may be carried out by cuff control module 20. If, on the other hand, no additional automatic measurement cycles were requested by the user at Step: 104 (Step: 110—No), control may proceed to Step: 112 where a user, such as a physician, may change or otherwise select an operating mode of system 10. For example, if the automatic operating mode was selected at Step: 104, a physician desiring to manually control various operations or components of system 10 may manipulate mode selector 38 to select either the manual operating mode or the hybrid operating mode. On the other hand, if, for example, the hybrid operating mode was previously selected at Step: 104, a physician desiring to manually inflate and/or manually deflate cuff 12 using manual cuff controller 32 may maintain system 10 in the hybrid operating mode, and Step: 112 may be omitted.

Control may then proceed to Step: 114 and Step: 116 where system 10 may be operated to determine further characteristics of artery 22. It is understood that in exemplary embodiments in which a physician desires to inflate cuff 12 manually, the physician may, at Step: 114, inflate cuff 12 to an occlusion pressure using manual cuff controller 32. Alternatively, if the physician desires assistance inflating cuff 12 during the manual operating mode or the hybrid operating mode, the physician may, during Step: 114, select, for example, one or more of a number of measurement cycles, an interval time between cycles, and a cuff inflation rate as described above with respect to Step: 106. In such embodiments, cuff control module 20 may control automatic cuff controller 16 to inflate cuff 12 during Step: 114.

Likewise, in exemplary embodiments in which the physician may, at Step: 116, desire assistance deflating cuff 12 during the manual operating mode or the hybrid operating mode, the physician may select, for example, a cuff deflation rate as described above. In such embodiments, cuff control module 20 may control automatic cuff controller 16 to deflate cuff 12 during Step: 116. As noted above, such assistance may be helpful to users of system 10 having difficulty manually inflating or deflating cuff 12.

Additionally, at Step: 114 and Step: 116 the physician may utilize sensor 18 and trigger 34 to determine one or more characteristics of artery 22. For example, regardless of whether the hybrid operating mode or the manual operating mode was selected at Step: 112, once artery 22 is substantially occluded at Step: 114 the physician may, using the valve associated with trigger 34, slowly begin to release air from cuff 12. Using a stethoscope or other like oratory device, the physician may listen for Korotkoff sounds indicative of blood beginning to flow through artery 22 using auscultatory methods known in the art. When such Korotkoff sounds are initially heard, the physician may manually actuate trigger 34, and sensor 18 may, in response, determine one or more desired characteristics associated with artery 22. For example, sensor 18 may determine the pressure associated with artery 22 at the time trigger 34 is actuated. Sensor 18 may then generate a signal indicative of the measured pressure and may direct such a signal to cuff control module 20. Cuff control module 20 may store the determined pressure (i.e., a systolic pressure) in the memory of cuff control module 20 and/or may display the determined pressure via communication module 24. Since sensor 18 determines the pressure associated with artery 22 at the time trigger 34 is actuated, embodiments of the present disclosure may advantageously avoid the time delay associated with, for example, the physician hearing Korotkoff sounds and responsively looking up to a manometer or other like device to visually observe a corresponding pressure reading.

At Step: 116, the physician may utilize the valve associated with trigger 34 to substantially deflate cuff 12, thereby substantially unoccluding artery 22. While continuing to listening for Korotkoff sounds indicative of the resumption of blood flow through artery 22, the physician may again actuate trigger 34 when no further sounds are heard. As described above, sensor 18 may again determine one or more desired characteristics associated with artery 22 in response to manual actuation of trigger 34. For example, sensor 18 may determine the pressure associated with artery 22 at the time trigger 34 is actuated, and may generate a signal indicative of the measured diastolic pressure. Sensor 18 may direct such a signal to cuff control module 20 indicative of the measured diastolic pressure. Cuff control module 20 may store the determined pressure in the memory of cuff control module 20 and/or may display the determined pressure via communication module 24.

At Step: 118, cuff control module 20 may utilize one or more of the characteristics determined at Steps: 106, 108, 114, and 116 to calculate and/or otherwise determine a hemodynamic parameter of patient 14. For example, information indicative of one or more such characteristics may be inputted into an algorithm, routine or program stored in memory of cuff control module 20, and processor 28 may determine an average blood pressure or other like hemodynamic parameter based on such characteristics. In additional exemplary embodiments, one or more algorithms may utilize the determined characteristics described above in combination with one or more empirically derived variables in determining the hemodynamic parameter. In such exemplary embodiments, the variable may be, for example, a scaling factor derived based on test data and/or other information associated with cuff 12 or based on predefined ranges of other parameters such as, for example, systolic and diastolic estimates or the time to inflate cuff 12. Such a variable may, for example, be derived based on an occlusion efficiency of cuff 12 or other known characteristics of system 10. In such exemplary embodiments, the variable may scale and/or otherwise affect the hemodynamic parameter determination, and a relatively large variable may result in a correspondingly large adjustment in the determined hemodynamic parameter.

At Step: 120, communication module 24 may output at least one of the characteristics determined at Steps: 106, 108, 114, and 116. At Step: 120, communication module 24 may also output one or more of the hemodynamic parameters determined at Step: 118. For example, as described above with respect to FIGS. 2-4, communication module 24 may simultaneously display the hemodynamic parameter and one or more of the characteristics determined at Steps: 106, 108, 114, and 116. Additionally, communication module 24 may display indicator 36 identifying which of the plurality of displayed characteristics was determined during the manual, automatic, or hybrid operating mode.

It is understood that by using the characteristics discussed above in determining a hemodynamic parameter of patient 14, the accuracy of such a determinations may be improved. For example, the methods described herein may reduce the error associated with such hemodynamic parameter determinations such that applicable medical device regulations may be satisfied. In particular, known auscultation systems require that a physician or other health care provider look up to visually observe a pressure reading as Korotokoff sounds are heard. The lag time associated with such systems results in measurement error that can reduce the accuracy of the ultimate hemodynamic parameter determination. On the other hand, since system 10 facilitates the determination of various characteristics at the instant Korotokoff sounds are heard, the lag time associated with known auscultation systems is avoided. Accordingly, the systems and methods described herein are more accurate and more reliable than existing systems.

Other embodiments of the present disclosure will be apparent to those skilled in the art from consideration of the specification and practice of the disclosure contained herein. For example, in additional exemplary embodiments, system 10 may comprise any known automated or manual auscultation system. In such exemplary embodiments, system 10 may further include one or more microphones or other like sound sensors configured to sense and/or otherwise detect auscultation signals associated with the artery 22. Accordingly, the methods described herein may be employed by either an oscillometric system or an auscultation system. It is understood that the various method steps described herein, and illustrated in exemplary FIG. 5, may be performed in any desirable order. It is intended that the specification and examples be considered as exemplary only, with a true scope and spirit of the present disclosure being indicated by the following claims.

What is claimed is:

1. A system for monitoring a patient, comprising:
   a sensor configured to determine a first characteristic and a second characteristic of an at least partially occluded artery; and
   a control module operable to control the sensor to perform a blood pressure measurement operation, the blood pressure measurement operation comprising a plurality of consecutive determinations of the first and second characteristics, wherein:
      the control module is operable in an automatic operating mode, a manual operating mode, and a hybrid operating mode,
      the automatic operating mode being characterized by the sensor determining, in response to one or more sensor control signals automatically generated by the control module, the first and second characteristics during at least one of automatic inflation and automatic deflation of a cuff associated with the control module,
      the manual operating mode being characterized by the sensor determining, in response to manual actuation of a trigger associated with the sensor, the first and second characteristics during at least one of inflation and deflation of the cuff, and
      controlling the sensor to perform the plurality of consecutive determinations of the first and second characteristics during the blood pressure measurement operation includes:
         receiving a selection of the manual operating mode or the hybrid operating mode,
         based at least in part on the selection, permitting at least one of manual inflation of the cuff and manual deflation of the cuff during the blood pressure measurement operation,
         controlling the sensor to determine a first subset of the plurality of consecutive determinations during the at least one of manual inflation of the cuff and manual deflation of the cuff,
         receiving, during the at least one of manual inflation of the cuff and manual deflation of the cuff, a control parameter governing at least one of automatic inflation of the cuff and automatic deflation of the cuff,
         based at least in part on receiving the control parameter and during the at least one of manual inflation of the cuff and manual deflation of the cuff, causing the control module to control at least one of automatic inflation of the cuff and automatic deflation of the cuff in accordance with the control parameter,
         controlling the sensor to determine a second subset of the plurality of consecutive determinations during the at least one of automatic inflation of the cuff and automatic deflation of the cuff, and
         determining a hemodynamic parameter of the patient based on the first and second subsets of the plurality of consecutive determinations.

2. The system of claim 1, wherein the first and second characteristics each comprise one of a systolic pressure, a diastolic pressure, and a mean arterial pressure.

3. The system of claim 1, wherein the hemodynamic parameter comprises one of a heart rate, a blood pressure, and an arterial stiffness.

4. The system of claim 1, wherein the trigger is operably connected to a valve configured to enable manual deflation of the cuff during the manual operating mode.

5. The system of claim 1, further comprising an automatic cuff controller configured to inflate and deflate the cuff in response to one or more cuff control signals generated by the control module.

6. The system of claim 5, wherein the one or more cuff control signals control, via the automatic cuff controller, at least one of a rate of inflation of the cuff, a rate of deflation of the cuff, a quantity of artery occlusion cycles, and a time interval between cycles.

7. The system of claim 1, further comprising a manual cuff controller associated with the trigger and fluidly connected to the cuff, the manual cuff controller being manually operable to direct pressurized air to the cuff for inflation of the cuff.

8. The system of claim 1, wherein:
the control module includes a mode selector configured to enable selection between the automatic operating mode, the manual operating mode, and the hybrid operating mode,
receiving the selection comprises receiving a selection of the hybrid operating mode via the mode selector, and
operation in the hybrid operating mode based at least in part on the selection of the hybrid operating mode is characterized by the sensor determining:
  at least part of the first subset of the plurality of consecutive determinations in response to one or more sensor control signals automatically generated by the control module, and
  a remainder of the first subset of the plurality of consecutive determinations in response to manual actuation of the trigger.

9. The system of claim 8, wherein based at least in part on the selection of the hybrid operating mode:
inflation of the cuff is performed automatically, and
deflation of the cuff is performed manually using a manual cuff controller fluidly connected to the cuff.

10. The system of claim 1, wherein the plurality of consecutive determinations comprises inflation of the cuff followed by deflation of the cuff, and causing the control module to control the at least one of automatic inflation of the cuff and automatic deflation of the cuff in accordance with the control parameter comprises a change in operation of the control module.

11. The system of claim 1, further comprising a communication module configured to simultaneously output a plurality of characteristics determined by the sensor including the first and second characteristics, the communication module being configured to output an indicator identifying which of the plurality of characteristics was determined during the automatic operating mode or the manual operating mode.

12. The system of claim 1, wherein in the hybrid operating mode, inflation of the cuff is performed automatically, and deflation of the cuff is performed manually using a manual cuff controller fluidly connected to the cuff.

13. The system of claim 1, further a communication module configured to display:
values corresponding to the first and second subsets of the plurality of consecutive determinations, and
an indicator identifying which of the values was determined during operation of the control module in the automatic operating mode, the manual operating mode, or the hybrid operating mode.

14. The system of claim 1, wherein determining the hemodynamic parameter of the patient comprises calculating the hemodynamic parameter with the first and second subsets of the plurality of consecutive determinations.

15. A method of determining a hemodynamic parameter of a patient, comprising:
a) selecting a manual operating mode or a hybrid operating mode associated with a control module of a patient monitoring system, the system including a sensor in communication with the control module, and a trigger in communication with the sensor;
b) substantially occluding an artery of the patient by manual operation of the patient monitoring system and while the control module is operating in the manual operating mode or the hybrid operating mode;
c) determining, with the sensor and while performing a blood pressure measurement operation, a first characteristic and a second characteristic associated with the artery while the artery is being substantially occluded by manual operation of the patient monitoring system, the blood pressure measurement operation comprising a plurality of consecutive measurements associated with the artery, and wherein each measurement of the plurality of consecutive measurements is characterized by substantial occlusion of the artery;
d) providing, while the artery is being substantially occluded during the manual operation of the patient monitoring system, a control parameter governing automatic operation of the control module;
e) during the manual operation of the patient monitoring system, causing the control module to substantially unocclude the artery, under automatic operation, and in accordance with the control parameter;
f) determining, with the sensor and while performing the blood pressure measurement operation, a third characteristic and a fourth characteristic associated with the artery while the artery is being substantially unoccluded by automatic operation of the control module; and
g) determining, with the control module, the hemodynamic parameter of the patient based on:
  at least one of the first and second characteristics, and
  at least one of the third and the fourth characteristics.

16. The method of claim 15, wherein the first characteristic comprises one of a systolic pressure and a diastolic pressure.

17. The method of claim 15, further including displaying a plurality of characteristics simultaneously with a communication module associated with the control module, the plurality of characteristics including the first characteristic, the second characteristic, the third characteristic, and the fourth characteristic.

18. The method of claim 17, further including displaying an indicator with the communication module, the indicator identifying which of the plurality of characteristics was determined during manual operation of the patient monitoring system or automatic operation of the control module.

19. The method of claim 15, wherein the operating parameter comprises one or more of a number of measurement cycles, an interval time between cycles, a cuff inflation rate, a cuff deflation rate, and a type of characteristic to be measured.

20. The method of claim 15, further including disposing an inflatable cuff circumferentially around a limb of the patient and proximate the artery, wherein substantially occluding the artery comprises manually inflating the cuff, and substantially unoccluding the artery comprises automatically deflating the cuff.

21. A method of determining a hemodynamic parameter of a patient, comprising:
a) selecting an operating mode associated with a control module of a patient monitoring system, the system including a sensor in communication with the control module, and a trigger in communication with at least one of the sensor and the control module;
b) manually inflating a cuff to an occlusion pressure while the control module is operating in the selected operating mode, wherein manually inflating the cuff at least partially occludes an artery of the patient;
c) manually deflating the cuff from the occlusion pressure to a deflated pressure less than the occlusion pressure;
d) determining, with the sensor, while performing a blood pressure measurement operation, during manual inflation or manual deflation of the cuff, and in response to manual actuation of the trigger, a first systolic pressure and a first diastolic pressure associated with the artery;

e) displaying the first systolic and first diastolic pressures via a communication module in communication with the control module;

f) selecting, during manual inflation or manual deflation of the cuff, a control parameter governing at least one of automatic inflation of the cuff and automatic deflation of the cuff by the control module;

g) based at least in part on the selecting, and during the manual inflation or manual deflation of the cuff, causing the control module to control the at least one of automatic inflation of the cuff and automatic deflation of the cuff;

h) automatically inflating the cuff to the occlusion pressure and under control of the control module, wherein automatically inflating the cuff at least partially occludes the artery;

i) automatically deflating the cuff, under control of the control module, from the occlusion pressure to the deflated pressure, wherein at least one of automatically inflating the cuff and automatically deflating the cuff is performed in accordance with the control parameter;

j) determining, with the sensor, while performing the blood pressure measurement operation, and under control of the control module, a second systolic pressure and a second diastolic pressure associated with the artery;

j) displaying the second systolic and second diastolic pressures via the communication module; and k) determining the hemodynamic parameter, with the control module, based on the first systolic pressure, the first diastolic pressure, the second systolic pressure, and the second diastolic pressure.

22. The method of claim 21, further including determining an average systolic pressure based on the first and second systolic pressures, and determining an average diastolic pressure based on the first and second diastolic pressures.

23. The method of claim 22, further including displaying the average systolic pressure and average diastolic pressure via the communication module.

24. The method of claim 23, further including displaying the average systolic pressure and average diastolic pressure simultaneously with at least one of the first systolic pressure, the first diastolic pressure, the second systolic pressure, and the second diastolic pressure.

25. The method of claim 23, further including displaying the first systolic pressure, the first diastolic pressure, the second systolic pressure, and the second diastolic pressure simultaneously via the communication module, and displaying an indicator via the communication module indicating that the second systolic pressure and second diastolic pressure were determined during manual inflation or manual deflation of the cuff.

26. The method of claim 21, further including:

determining at least one of a pulse oxidation and a heart rate of the patient under the control of the control module, displaying the at least one of the pulse oxidation and the heart rate via the communication module, and displaying the at least one of the pulse oxidation and the heart rate simultaneously with at least one of the first systolic pressure, the first diastolic pressure, the second systolic pressure, and the second diastolic pressure.

27. The method of claim 21, wherein the blood pressure measurement operation includes inflating the cuff followed by deflating the cuff.

28. The method of claim 26, further including l) determining an average systolic pressure based on the first systolic pressure and the second systolic pressure, m) determining an average diastolic pressure based on the first diastolic pressure and the second diastolic pressure, and n) displaying the average systolic pressure and the average diastolic pressure simultaneously with the at least one of the pulse oxidation and the heart rate.

* * * * *